(12) United States Patent
Warner (10) Patent No.: US 11,376,129 B2
(45) Date of Patent: Jul. 5, 2022

(54) APPARATUSES FOR DISTAL FIBULA REPLACEMENT AND RELATED METHODS

(71) Applicant: Hayward Surgical, L.L.C., Baton Rouge, LA (US)

(72) Inventor: Meredith Warner, Baton Rouge, LA (US)

(73) Assignee: Hayward Surgical, L.L.C., Baton Rouge, LA (US)

( * ) Notice: Subject to any disclaimer, the term of this patent is extended or adjusted under 35 U.S.C. 154(b) by 289 days.

(21) Appl. No.: 16/665,716

(22) Filed: Oct. 28, 2019

(65) Prior Publication Data
US 2020/0054458 A1 Feb. 20, 2020

Related U.S. Application Data

(63) Continuation-in-part of application No. 15/786,327, filed on Oct. 17, 2017, now Pat. No. 10,456,266.
(Continued)

(51) Int. Cl.
*A61F 2/42* (2006.01)
*A61F 2/30* (2006.01)
*A61F 2/08* (2006.01)

(52) U.S. Cl.
CPC ........ *A61F 2/4202* (2013.01); *A61F 2/30749* (2013.01); *A61F 2002/0852* (2013.01);
(Continued)

(58) Field of Classification Search
CPC ............ A61F 2/42; A61F 2/4202; A61F 2/30; A61F 2/30749; A61F 2002/0852;
(Continued)

(56) References Cited

U.S. PATENT DOCUMENTS 5,116,380 A * 5/1992 Hewka ................ A61F 2/30724
623/23.25
5,190,544 A * 3/1993 Chapman ........... A61B 17/8061
606/280
(Continued)

FOREIGN PATENT DOCUMENTS

CN 102772242 B 9/2014
CN 203873860 U 10/2014

OTHER PUBLICATIONS

Di Domenico, et al., "Total Ankle Replacement with a Staged Correction of a 20 Degree Post Traumatic Ankle Valgus and Medial Ankle Instability", Case Report, Clin Res Foot Ankle, vol. 4, Issue 1 (1000178), 2016, 4 pages.
(Continued)

*Primary Examiner* — Yashita Sharma
(74) *Attorney, Agent, or Firm* — McGlinchey Stafford PLLC; R. Andrew Patty, II (57) ABSTRACT

Apparatuses for distal fibula replacement and related methods are described herein. The apparatus generally includes an implantable stem component including a proximal portion that is contoured to have an anterior overlap with a portion of a fibula bone of a patient, and a distal portion that defines one or more channels configured to receive one or more tendons of the patient. Related methods include placing the apparatus on the portion of the fibula bone of the patient.

20 Claims, 8 Drawing Sheets

Related U.S. Application Data (60) Provisional application No. 62/543,689, filed on Aug. 10, 2017.

(52) U.S. Cl.
CPC ............... *A61F 2002/30405* (2013.01); *A61F 2002/30787* (2013.01); *A61F 2002/421* (2013.01)

(58) Field of Classification Search
CPC ............ A61F 2002/30405; A61F 2002/30787; A61F 2002/421; A61F 2/3094; A61F 2/30965; A61F 2002/30784; A61F 2002/30957; A61F 2002/30985; A61B 17/00; A61B 17/74; A61B 17/56; A61B 17/80
USPC ....... 623/21.18; 606/61, 69, 70, 71, 80, 280, 606/283, 286, 297
See application file for complete search history.

(56) References Cited

U.S. PATENT DOCUMENTS

| | | | |
|---|---|---|---|
| 5,868,749 A * | 2/1999 | Reed | A61B 17/80 606/76 |
| 7,537,596 B2 | 5/2009 | Jensne | |
| 7,731,718 B2 | 6/2010 | Schwammberger et al. | |
| 7,799,061 B2 | 9/2010 | Kay et al. | |
| 8,118,848 B2 | 2/2012 | Ducharme et al. | |
| 8,177,822 B2 | 5/2012 | Tellman et al. | |
| 2009/0275991 A1 * | 11/2009 | Medoff | A61B 17/8061 606/297 |
| 2013/0218282 A1 | 8/2013 | Hunt | |
| 2015/0289910 A1 | 10/2015 | Alireza | |
| 2016/0262814 A1 | 9/2016 | Wainscott | |
| 2016/0278828 A1 | 9/2016 | Ragghianti | |

OTHER PUBLICATIONS

Synthes article, "3.5 mm and 4.5 mm Curved Locking Compression Plates (LCP)", Synthes, 2009, 40 pages.

* cited by examiner

APPARATUSES FOR DISTAL FIBULA REPLACEMENT AND RELATED METHODS

CROSS-REFERENCE TO RELATED APPLICATIONS

This application is a continuation-in-part of and commonly owned U.S. application Ser. No. 15/786,327, filed on Oct. 17, 2017, which claims priority of commonly owned U.S. provisional patent application No. 62/543,689, filed on Aug. 10, 2017. Each patent application identified above is incorporated here by reference in its entirety to provide continuity of the disclosure.

TECHNICAL FIELD

The present disclosure relates to apparatuses or methods for treatment of bones or joints. In particular, the present disclosure relates to apparatuses specially adapted for distal fibula replacement in a patient, and related methods.

BACKGROUND

Total ankle arthroplasty (TAA), also known as total ankle replacement, is a surgical procedure that orthopaedic surgeons use to treat ankle arthritis, which may be a result of normal wear and tear due to aging or from an injury (e.g., a broken ankle or dislocation). TAA is generally performed either under general anesthetic or nerve block. A tourniquet is used at the time of surgery to control bleeding and improve visualization during the surgery. The ankle is approached from the front or the side depending on the type of implant being used. Bone is then cut, allowing for placement of the metal and plastic components that re-create the ankle joint. Sometimes the patient may have a tight calf muscle or tight Achilles tendon that requires lengthening to improve range of motion of the ankle. The wounds are then closed using stitches or staples, and a splint is applied.

However, in patients in which a distal fibula has been removed or is not present for some reason, TAA is typically contraindicated. Further, both TAAs and rates of ankle arthritis appear to be becoming more common. Thus, there is a need in the art for apparatuses and related methods that can serve as a replacement for a distal fibula in patients in which the distal fibula has been removed or is not present for some reason, to facilitate TAA or other procedures in which the presence of a fibula is required or desirable.

Contained herein is a disclosure directed to resolving, or at least reducing, one or more of the problems mentioned above, or other problems that may exist in the art.

NON-LIMITING BRIEF SUMMARY OF THE INVENTION

The present disclosure relates to apparatuses specially adapted for distal fibula replacement in a patient, and related methods. The apparatus generally comprises an implantable stem component comprising a proximal portion and a distal portion. The proximal portion is contoured to form an anterior overlap for engaging with a portion of a fibula bone. The distal portion defines one or more channels positioned and contoured to operatively receive one or more tendons of the patient. The proximal portion further defines one or more holes, each of the one or more holes configured to direct a respective connector when extending therethrough so as to affix the proximal portion to the portion of the fibula bone when installed on the patient. The apparatus further defines one or more apertures, each aperture configured to direct a respective connector when extending therethrough so as to affix the apparatus to a syndesmosis when the apparatus is installed on the patient.

One or more aspects of the invention include the apparatus of the preceding paragraph, wherein the proximal portion is an elongated body.

One or more aspects of the invention include the apparatus of any preceding paragraph, wherein each channel includes a posterior inlet and an anterior outlet.

One or more aspects of the invention include the apparatus of any preceding paragraph, wherein each of the one or more apertures is configured to direct its respective connector at an angle in the range of about 15° to about 35° anterior to a coronal plane of the patient.

One or more aspects of the invention include the apparatus of any preceding paragraph, wherein each of the one or more channels is textured and contoured so as to accommodate the peronaeus brevis tendon when the apparatus is configured to be installed on the patient.

One or more aspects of the invention include the apparatus of any preceding paragraph, wherein each of the one or more channels is textured and contoured so as to accommodate the peronaeus longus tendon when the apparatus is installed on the patient.

One or more aspects of the invention include the apparatus of any preceding paragraph, wherein each respective connector is a screw.

One or more aspects of the invention include the apparatus of any preceding paragraph, wherein the apparatus is configured to replace a portion of the distal fibula when the apparatus is configured to be installed on the patient.

One or more aspects of the invention include the apparatus of any preceding paragraph, wherein the apparatus is configured to act as a lateral buttress within a mortise to confine a talus or a talar replacement device.

One or more aspects of the invention include the apparatus of any preceding paragraph, wherein each respective connector has a diameter in the range of about 2.7 mm to about 4.0 mm.

One or more aspects of the invention include the apparatus of any preceding paragraph, wherein the respective connector for each of the one or more apertures is either a soft tissue fixation device or a screw.

One or more aspects of the invention include the apparatus of any preceding paragraph, wherein the distal portion forms a groove disposed so as to accept and accommodate the peroneal tendons of the patient when the apparatus is configured to be installed on the patient.

One or more aspects of the invention include the apparatus of any preceding paragraph, wherein each of the one or more channels is textured and contoured so as not to promote adhesions or irritation of its respective tendon when the apparatus is installed on the patient.

One or more aspects of the invention include the apparatus of any preceding paragraph, wherein the apparatus comprises a polymer coating.

One or more aspects of the invention include the apparatus of the preceding paragraph, wherein the polymer coating is provided on the surface of the distal portion of the apparatus.

One or more aspects of the invention include the apparatus of any preceding paragraph, wherein the distal portion defines two channels positioned and contoured to operatively receive one or more tendons of the patient.

One or more aspects of the invention include the apparatus of any preceding paragraph, wherein the distal portion defines a single position channel positioned and contoured to operatively receive one or more tendons of the patient.

One or more aspects of the invention include the apparatus of any preceding paragraph, wherein each of the one or more channels has an angle from superior posterior to distal anterior in the range of about 20 degrees to about 70 degrees.

Another aspect of the invention provides a method comprising placing an apparatus of any preceding paragraph so that a proximal portion of the apparatus has anterior overlap with a portion of a fibula bone of a patient. In an aspect, the method includes placing one or more screws through apparatus so as to affix the apparatus to the portion of the fibula bone.

While multiple aspects are disclosed, still other aspects of the invention will become apparent to those skilled in the art from the following detailed description. As will be apparent, certain aspects, as disclosed herein, are capable of modifications in various obvious aspects, all without departing from the spirit and scope of the claims as presented herein. Accordingly, the drawings and detailed description are to be regarded as illustrative in nature and not restrictive.

BRIEF DESCRIPTION OF THE SEVERAL VIEWS OF THE DRAWINGS

The claimed subject matter may be understood by reference to the following description taken in conjunction with the accompanying figures, in which like reference numerals identify like elements, and in which:

The accompanying drawings illustrate specific embodiments of that which is the subject of this disclosure. However, it is to be understood that these embodiments are not intended to be exhaustive, nor limiting of the disclosure. These specific embodiments are but examples of some of the forms in which the disclosure may be practiced. Like reference numbers or symbols employed across the several figures are employed to refer to like parts or components illustrated therein.

DETAILED DESCRIPTION

Disclosed herein are apparatuses specially adapted for replacing all or a portion of a distal fibula of a patient, and related methods. For example, the apparatuses disclosed herein may be employed in a patient for loss of all or a portion of a fibula bone from tumor or trauma.

With reference to FIGS. 1-4, the apparatus 100 comprises an implantable stem component comprising a proximal portion 110 and a distal portion 120. The proximal portion 110 of the apparatus 100 is contoured to form an anterior overlap for engaging with a portion of a fibula bone 200 of a patient, for example, a lateral portion of a fibula bone 200 of a patient. In an aspect the implantable stem component is configured to engage the intramedullary canal of the remnant fibula. In one or more embodiments, for example as illustrated in FIG. 1A and FIG. 2A, the proximal portion 110 has a curved or an arcuate profile on both its upper surface 111 and the lower surface 112. The lower surface 112 mates with the portion of the fibula bone 200. For example, the proximal portion 110 is an elongated body (e.g., an elongated plate) that has a profile substantially conforming to the portion of a distal fibula of a human.

Figures 1, 1A:
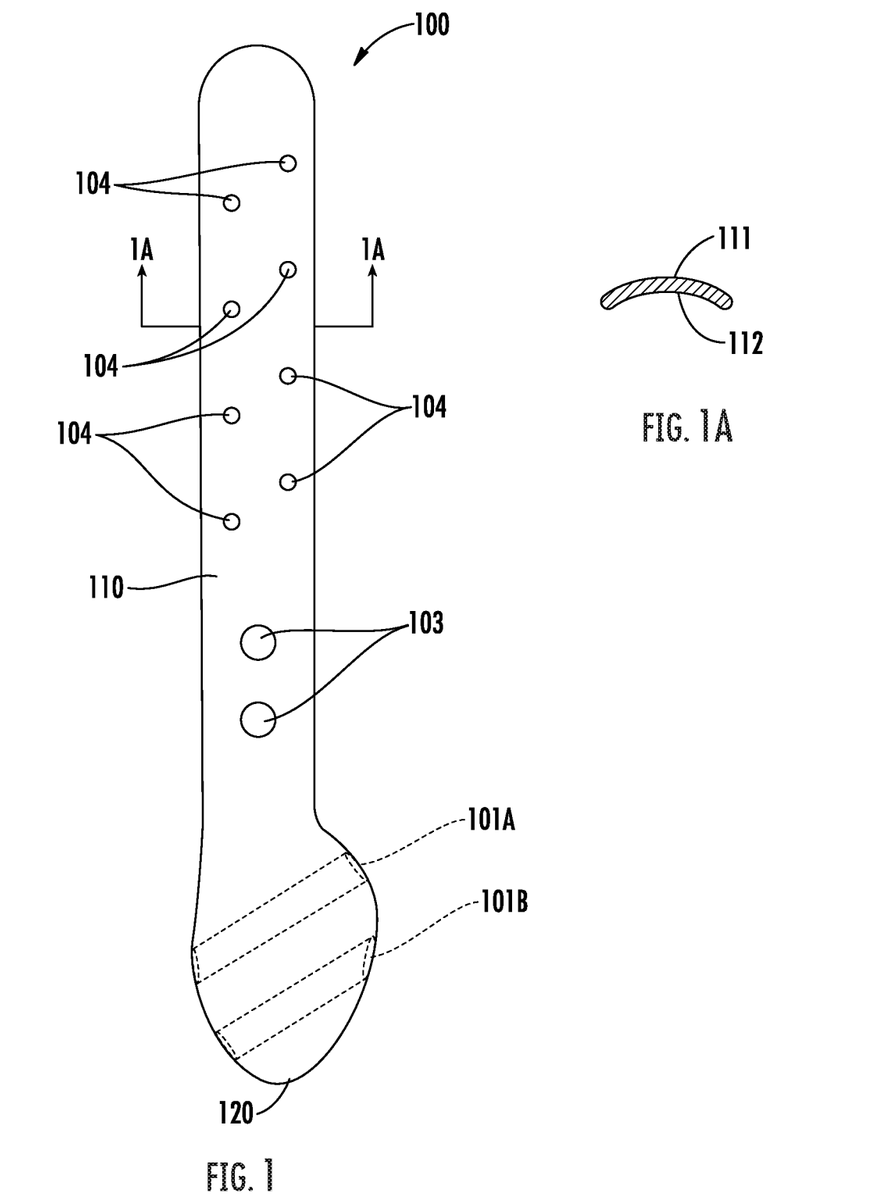
FIG. 1 illustrates an apparatus in accordance with one aspect of this invention.
FIG. 1A illustrates a cross-sectional view along line 1A of the apparatus illustrated in FIG. 1.
Figures 2, 2A:
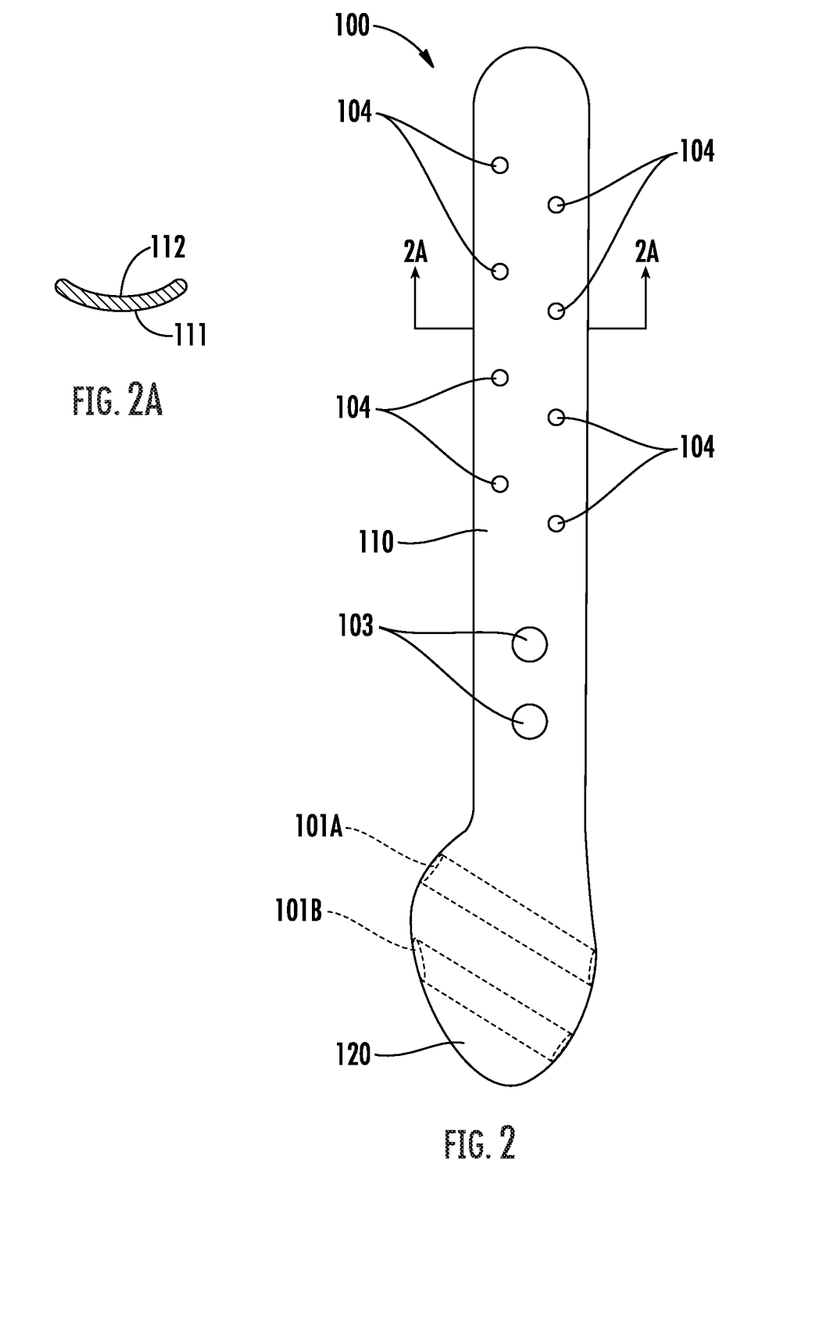
FIG. 2 illustrates an opposed view of the apparatus illustrate in FIG. 1.
FIG. 2A illustrates a cross-sectional view along line 2A of the apparatus illustrated in FIG. 2.

The proximal portion 110 of the apparatus 100 defines one or more holes 104. Each hole is configured to direct a respective connector 105 when extending therethrough so as to affix the proximal portion 110 of the apparatus 100 to the portion of the fibula bone 200 (e.g., lateral portion of the fibula bone) when installed on the patient. The one or more holes 104 may be positioned on the proximal portion 110 in any location suitable to affix the proximal portion 110 of the apparatus 100 to the fibula bone. For example, as shown in FIG. 1, the holes 104 may be disposed in a staggered arrangement, such as on opposing sides of a central axis of the proximal portion 110 of the apparatus 100, to direct connectors 105 along staggered, nonparallel paths, which increases distances between successive connectors 105 and can reduce the likelihood of fissuring the fibula bone longitudinally. Alternatively, in one or more embodiments, the holes 104 can be arrayed generally in a line along the proximal portion 110, for example, centered across the width of the proximal portion 110. Each of the one or more holes 104 can be a variable angle hole with a variance of up to about 5 degrees offset from a plane that is perpendicular the longitudinal axis of the proximal portion of the apparatus 100.

Each respective connector 105 for each hole 104 has a diameter in the range from about 2.5 mm to about 4.0 mm. Each hole 104 has a diameter in the range from about 2.5 mm to about 3.8 mm. Each hole 104 and its respective connector 105 are preferably sized and configured so that the head of the connector 105 mates with and sits substantially flush with the hole 104. The one or more holes 104 defined by the proximal portion 110 of the apparatus 199 can be threaded or non-threaded depending upon the particular surgical procedure. In an aspect, the one or more holes 104 are threaded with a variable pitch. The respective connector 105 for each hole 104 can be any conventional connector known in the art including without limitation locking screws, and non-locking screws, for example, SYNTHES® locking screws and non-locking screws with diameters of 2.5, 2.7 mm, 3.5 mm and/or 4.0 mm.

The apparatus 100 further defines one or more apertures 103. Each of the one or more apertures 103 is configured to direct a respective connector when extending therethrough so as to affix the apparatus to a syndesmosis region and tibia when the apparatus is installed on the patient. Each aperture 103 directs its respective connector at an angle in the range of about 15° to about 35°, more preferably about 20° to about 30°, posterior to anterior to a coronal plane of the patient. Each aperture 103 may be threated or unthreaded, and has a diameter in the range from about 3.8 mm to about 5 mm, or in the range from about 3.8 mm to about 4.8 mm. When the apparatus 100 is installed on a patient, each of the connector should be directed through its respective aperture 103 so that the connector is positioned so as to be parallel or substantially parallel to the ankle joint of the patient in the coronal plane and angled in the sagittal plane (posterior to anterior). The apertures 103 may be positioned on the apparatus 100 in any location suitable to affix the apparatus 100 to the tibia bone at the syndesmosis region. For example, in one or more embodiments, the apparatus defines at least two apertures, which are about 4 cm and 5 cm, respectively, from the most distal aspect of the apparatus 100, and the at least two apertures 103 are arrayed in a parallel line along the apparatus 100.

Each respective connector for each aperture 103 has a diameter in the range from about 2.7 mm to about 4.0 mm. Each aperture 103 and its respective connector are preferably sized and configured so that the head of the connector mates with the aperture 103 so the head of the connector sits substantially flush with the aperture 103. The one or more apertures 103 defined by the apparatus can be threaded or non-threaded depending upon the particular surgical procedure. The respective connector for each aperture 103 can be any conventional connector known in the art including without limitation a screw as described above or soft tissue fixation device, for example, suture anchor such as a TIGHTROPE® fixation available from Arthrex Inc. having a business address of 1370 Creekside Boulevard, Naples, Fla. 34108-1945, a standard surgical screw, for example, SYNTHES® locking screws and non-locking screws with diameters of 2.7 mm, 3.5 mm and/or 4.0 mm.

The distal portion 120 of the apparatus is shaped like the distal end of a fibula of a person. The distal portion can also provide a lateral buttress to a talar replacement device. In an aspect, the distal portion 120 of the apparatus is configured to receive one or more tendons 301 of the patient. The distal portion 120 defines one or more channels 101 configured to receive one or more tendons 301 of the patient when the apparatus is installed on the patient. For example, as illustrated FIGS. 1-4, in one or more embodiments, the distal portion defines a first channel 101A configured to receive a peronaeus brevis tendon of the patient when the apparatus is installed on the patient, and further defines a second channel 101B configured to receive a peronaeus longus tendon of the patient when the apparatus is installed on the patient. The distal portion 120 of the apparatus 100 also forms a groove 121 disposed so as to accept and accommodate the peroneal tendons of the patient when the apparatus is installed on the patient. Each channel 101A, 101B includes a posterior inlet and an anterior outlet. Each channel 101A, 101B is also textured and contoured so as to accommodate and minimize damage to its respective tendon. For example, in one or more embodiments, each channel 101A, 101B has beveled edges so as not to promote tearing or irritation of the tendon. Each channel 101A, 101B preferably has a gentle angle from superior posterior to distal anterior to simulate the natural direction of the tendon. For example, in one or more embodiments, the first channel 101A has a gentle angle α of about 35 degrees to about 55 degrees, more preferably about 40 degrees to about 50 degrees, and the second channel 101B has a gentle angle of about 25 degrees to about 45 degrees, more preferably about 30 degrees to about 40 degrees. Each channel 101A, 101B should be smooth so as not to promote adhesions or tendon irritation and to allow normal excursion. Each channel 101A, 101B has a diameter of about 5 mm to about 8 mm.

Alternatively, as illustrated FIGS. 5-8, in an aspect, the distal portion 120 may define one or more channels (e.g., a single channel) 101 configured to receive one or more tendons of the patient (e.g., a peronaeus brevis tendon of the patient, a peronaeus longus tendon of the patient, or both) when the apparatus is installed on the patient. The distal portion 120 of the apparatus 100 may also define a groove 121 disposed so as to accept and accommodate the one or more tendons 301 of the patient when the apparatus is installed on the patient. The channel 101 includes a posterior inlet and an anterior outlet, should be positioned and contoured so as to accommodate and minimize damage to its respective tendon. For example, the channel should be smooth so as not to promote adhesions or tendon irritation and to allow normal excursion. The channel a diameter of about 5 mm to about 8 mm. Further, the channel 101 preferably has a gentle angle α from superior posterior to distal anterior to simulate the natural direction of the tendon. For example, in one or more embodiments, the channel has a gentle angle of about 20 degrees to about 70 degrees, more preferably about 35 degrees to about 55 degrees, more preferably about 40 degrees to about 50 degrees.

Figure 3:
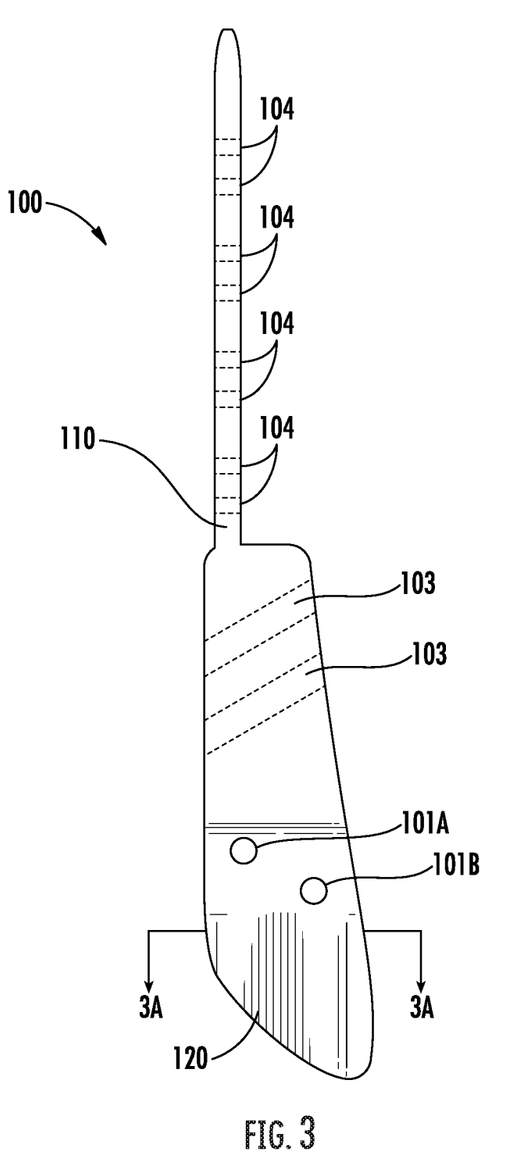
FIG. 3 illustrates a posterior view of the apparatus illustrated in FIG. 1.
Figure 3A:
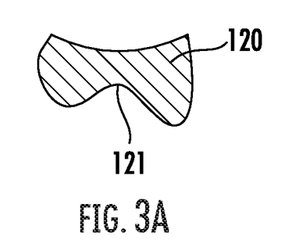
FIG. 3A illustrates a cross-sectional view along line 3A of the apparatus illustrated in FIG. 3.
Figure 3B:
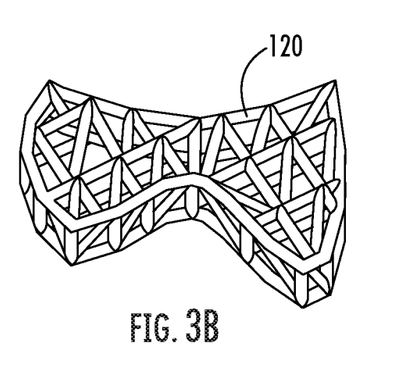
FIG. 3B illustrates a cutaway of the view illustrated in FIG. 3A.
Figure 7:
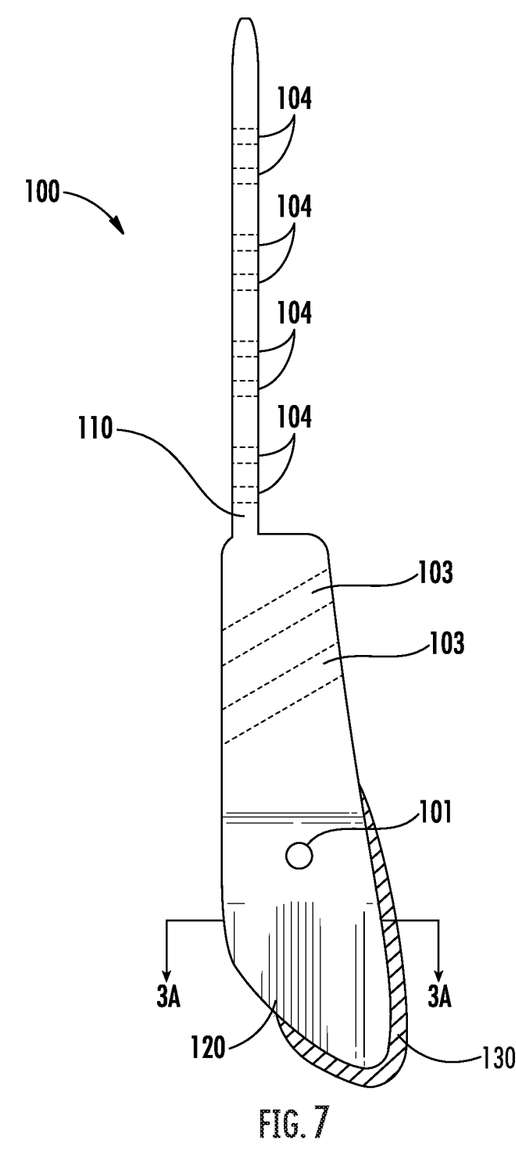
FIG. 7 illustrates a posterior view of the apparatus illustrated in FIG. 5.
Figure 7A:
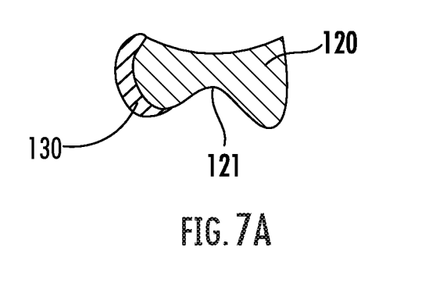
FIG. 7A illustrates a cross-sectional view along line 7A of the apparatus illustrated in FIG. 7.
Figure 7B:
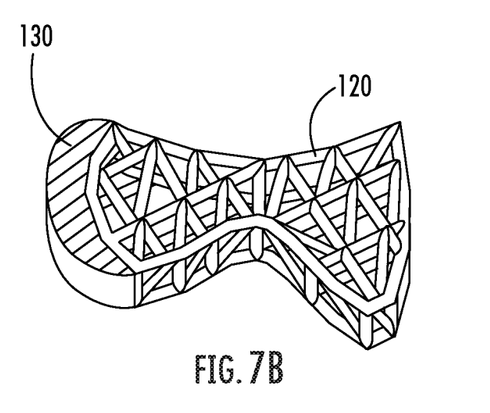
FIG. 7B illustrates a cutaway view of the view illustrated in FIG. 7A.
Figure 8:
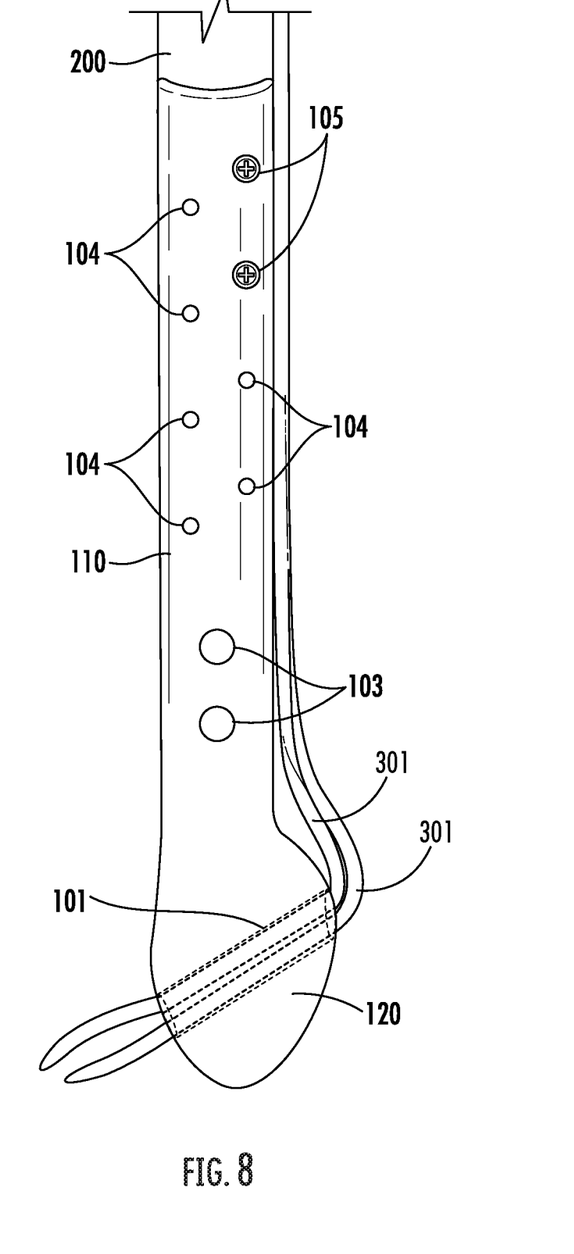
FIG. 8 illustrates the apparatus illustrated in FIG. 5 during installation procedure of the apparatus on a portion of a fibula bone of a patient.

In one or more embodiments, for example as illustrated in FIG. 3B and FIG. 7B, the distal portion 120 of the apparatus 100 may comprise a cage-like member including a substantially hollow body with one or more supporting struts, which can provide additional advantages such as decreasing the overall weight of the apparatus, reducing material costs. For example, the distal portion 120 of the apparatus 100 can be constructed from using three dimensional printing techniques and milling methods. Alternatively, the distal portion 120 of the apparatus 100 may be formed as a solid member or hollow member. For example, the distal portion of the apparatus can be constructed using molding methods.

In one or more embodiments, the apparatus comprises a polymer coating. The polymer coating can reduce or prevent damage or irritation that may be caused as a result of the interaction of the apparatus with body of the patient. For example, as illustrated in FIG. 6, FIG. 7, FIG. 7A and FIG. 7B, at least a portion of medial side of the distal portion of the apparatus may comprise a polymer coating 130. The polymer coating may any suitable coating having a low frictional coefficient (e.g., frictional coefficient similar to cartilage or ceramic) so as to not interact adversely with the metal of the associated total ankle implant, for example, a non-metallic biocompatible material. In an aspect, the polymer coating comprises one selected from the group consisting of polyethylene, ceramic, carbon fiber, and any combination of two or more of the foregoing. It should be appreciated that the polymer coating may be formed on, joined or adhered to the surface of the apparatus according to methods known to those of ordinary skill in the art. The polymer coating may have a thickness in the range of from about 1 mm to about 4 mm.

The apparatus 100 can also be configured to act as a lateral buttress within a mortise to confine a talus or a talar replacement device. For example, the same or similar anatomic approach and application could be used for the distal fibular replacement to buttress a total ankle replacement, talus, or talar replacement.

The apparatus 100 can be sized and configured based on details of the patient the apparatus is to be installed upon, for example, the dimensions of the apparatus 100 can be adapted based on the sex of the patient (e.g., male or female), bone length of the distal fibula patient, and so forth. For example, in an aspect, the length of the apparatus is in the range of from about 12 cm to about 18 cm. The length of the apparatus may be in the range of from about 12 cm to about 14 cm. The length of the apparatus may be in the range of from about 14 cm to about 16 cm. The length of the apparatus may be in the range of from about 16 to about 18 cm. In an aspect, the width of the proximal portion of the apparatus is in the range of from about 1.0 cm. to about 1.4 cm. In an aspect, width of the distal portion of the apparatus is in the range of from about 2.0 cm to about 2.5 cm, and the thickness of the distal portion of the apparatus may be about 1.0 cm.

Figure 4:
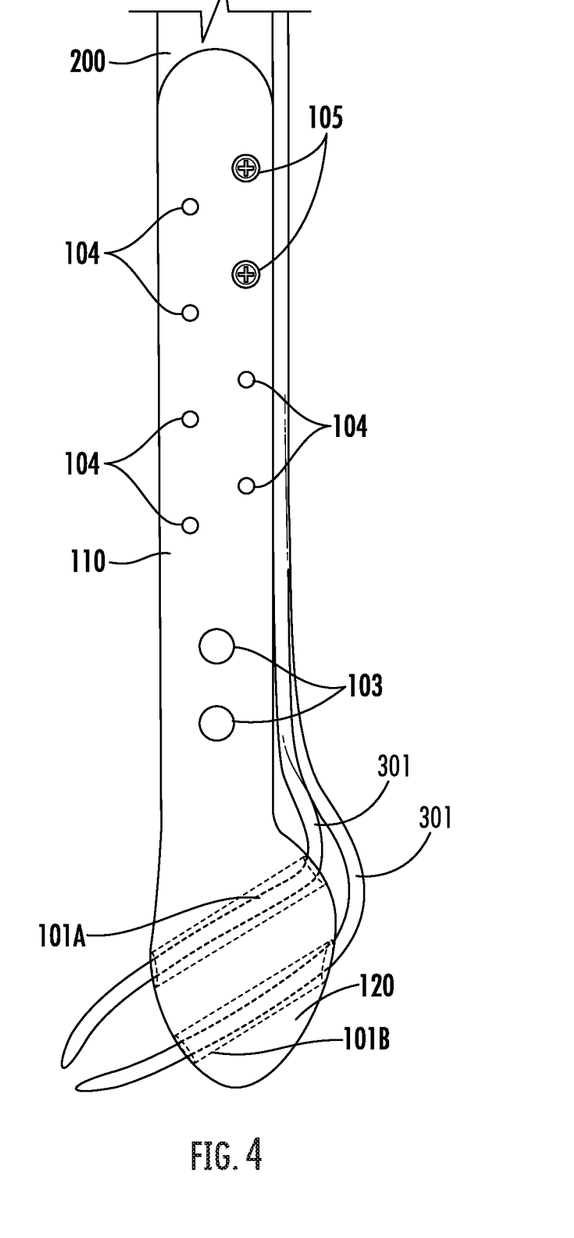
FIG. 4 illustrates the apparatus illustrated in FIG. 1 during installation procedure of the apparatus on a portion of a fibula bone of a patient.
Figure 5:
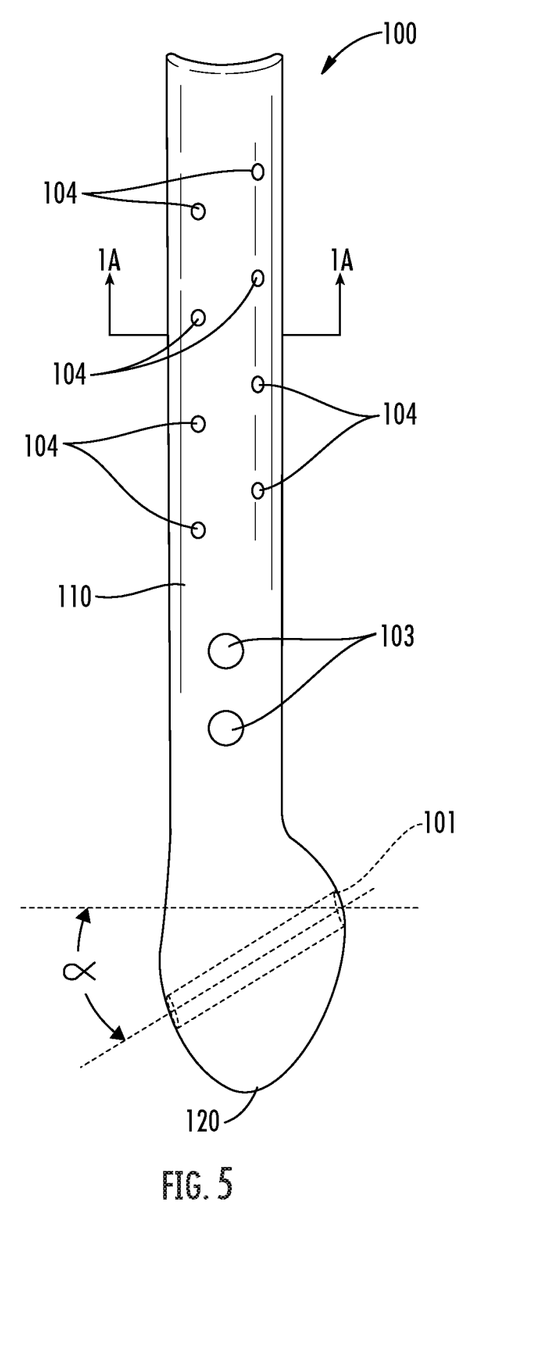
FIG. 5 illustrates an apparatus in accordance with one aspect of this invention.
Figure 5A:
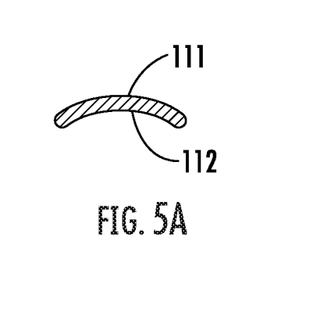
FIG. 5A illustrates a cross-sectional view along line 5A of the apparatus illustrated in FIG. 5.
Figure 5B:
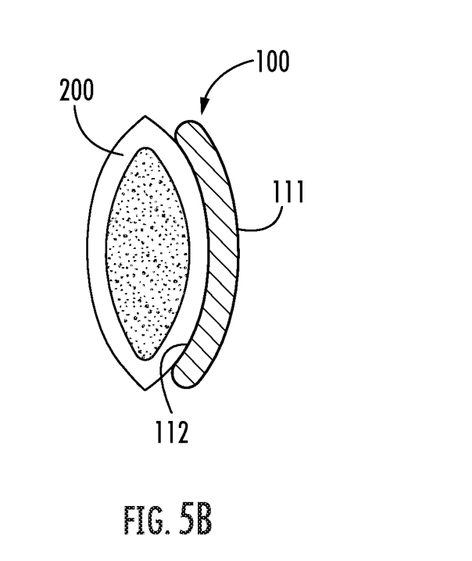
FIG. 5B illustrates a top view of the apparatus illustrated in FIG. 5 during installation procedure of the apparatus on a portion of a fibula bone of a patient.
Figures 6, 6A:
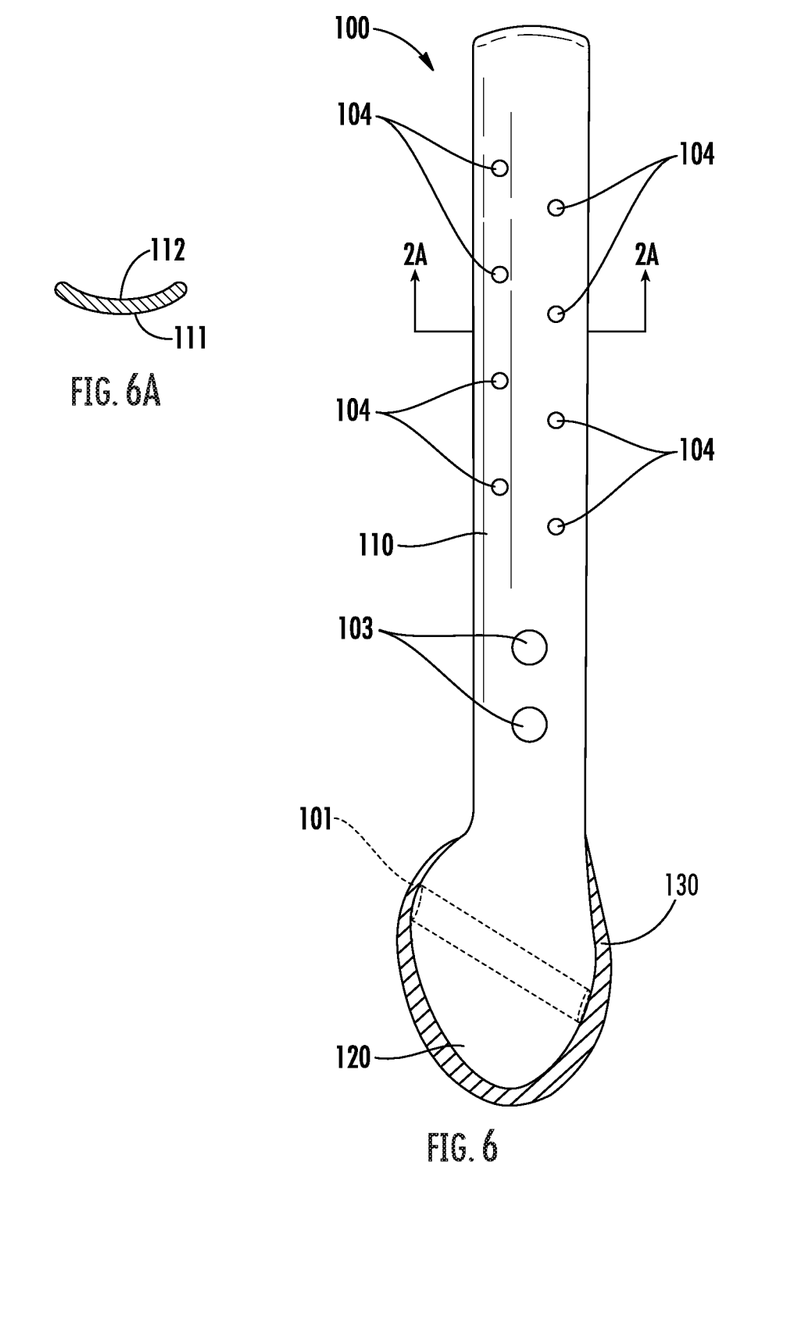
FIG. 6 illustrates an opposed view of the apparatus illustrate in FIG. 5.
FIG. 6A illustrates a cross-sectional view along line 6A of the apparatus illustrated in FIG. 6.

In an implant operation, the apparatus 100 for distal fibula replacement is placed so that the proximal portion 110 of the apparatus 100 has anterior overlap with a portion of the fibula bone 200 of the patient, for example, as illustrated in FIG. 4. One or more connectors 105 are then placed through the apparatus 100 so as to affix the apparatus 100 to the portion of the fibula bone 200 of the patient. For example, in one or more embodiments, a screw can be placed (e.g., by drilling) through a respective hole 104 of the proximal portion of the apparatus 100, which directs its respective connector 105 when extending therethrough so as to proximal portion 110 to the portion of the fibula bone 200 when installed on a patient. In one or more embodiments, one or more connectors can also be placed through the one or more respective apertures 103 of the apparatus into the syndesmosis region and tibia of the patient. For example, a screw or soft tissue fixation device can be placed through a respective aperture 103 of the apparatus 100, which directs its respective connector when extending therethrough at an angle in the range of about 20° to about 30° anterior to a coronal plane of the patient, which affixes the apparatus 100 to the syndesmosis region of the patient and provides a stable connection to the tibia.

In one or more embodiments, the tendons could be split at about 20% to about 50% on the long axis from anywhere along the tendon (myotendinous junction to insertion point). The split tendons could then be transected, either distally or proximally, depending on surgical conditions. The free end of the tendons could then be threaded through the one or more channels 101. For example, in FIG. 4 the free end of one or more tendons 301 may be threaded through the appropriate channel 101A, 101B of the apparatus 100. For example, the peroneaus brevis tendon of the patient is threaded through the first channel 101A defined by the distal portion 120 of the apparatus 100, and the peroneaus longus tendon of the patient is also threaded through the second channel 102A defined by the distal portion 120 of the apparatus 100. As another example, in FIG. 8, the free end of the one or more tendons 301 may be threaded through a single channel 101. Once the tendon is in the appropriate channel, its free end could then be attached to the foot or ankle by means of staple, tenodesis screw, suture anchor or suture. This configuration should then allow the device to provide both a static buttress and a dynamic ligamentous support system for the lateral aspect of the foot and ankle.

It should be recognized that unless stated otherwise, it is intended that endpoints are to be interchangeable. Further, any ranges include iterative ranges of like magnitude falling within the expressly stated ranges or limitations disclosed herein is to be understood to set forth every number and range encompassed within the broader range of values. It is to be noted that the terms "range" and "ranging" as used herein generally refer to a value within a specified range and encompasses all values within that entire specified range.

Except as may be expressly otherwise indicated, the article "a" or "an" if and as used herein is not intended to limit, and should not be construed as limiting, a claim to a single element to which the article refers. Rather, the article "a" or "an" if and as used herein is intended to cover one or more such elements, unless the text taken in context clearly indicates otherwise.

Each and every patent or other publication or published document referred to in any portion of this specification is incorporated as a whole into this disclosure by reference, as if fully set forth herein.

This invention is susceptible to considerable variation in its practice. Therefore the foregoing description is not intended to limit, and should not be construed as limiting, the invention to the particular exemplifications presented hereinabove.

What is claimed is:

1. An apparatus for distal fibula replacement in a patient, the apparatus comprising:
   an implantable stem component comprising a proximal portion and a distal portion;
   wherein the proximal portion is contoured to form an anterior overlap for engaging with a portion of a fibula bone;
   wherein the distal portion defines one or more channels positioned and contoured to operatively receive one or more tendons of the patient, each of the one or more channels having an angle from superior posterior to distal anterior in the range of about 20 degrees to about 70 degrees;
   wherein the proximal portion defines one or more holes, each of the one or more holes configured to direct a respective connector when extending therethrough so as to affix the proximal portion to the portion of the fibula bone when installed on the patient; and
   wherein the apparatus further defines one or more apertures, each aperture configured to direct a respective connector when extending therethrough so as to affix the apparatus to a syndesmosis when the apparatus is installed on the patient.

2. The apparatus of claim 1, wherein the proximal portion is an elongated body.

3. The apparatus of claim 1, wherein each of the one or more channels comprises a posterior inlet and an anterior outlet.

4. The apparatus of claim 1, wherein each of the one or more apertures is configured to direct its respective connector at an angle in the range of about 15° to about 35° anterior to a coronal plane of the patient.

5. The apparatus of claim 1, wherein each of the one or more channels is textured and contoured so as to accommodate the peroneaus brevis tendon when the apparatus is configured to be installed on the patient.

6. The apparatus of claim 1, wherein each of the one or more channels is textured and contoured so as to accommodate the peronaeus longus tendon when the apparatus is installed on the patient.

7. The apparatus of claim 1, wherein each respective connector is a screw.

8. The apparatus of claim 1, wherein the apparatus is configured to replace a portion of the distal fibula when the apparatus is configured to be installed on the patient.

9. The apparatus of claim 1, wherein the apparatus is configured to act as a lateral buttress within a mortise to confine a talus or a talar replacement device.

10. The apparatus of claim 1, wherein each respective connector has a diameter in the range of about 2.7 mm to about 4.0 mm.

11. The apparatus of claim 1, wherein the respective connector for each of the one or more apertures is either a soft tissue fixation device or a screw.

12. The apparatus of claim 1, wherein the distal portion forms a groove disposed so as to accept and accommodate the peroneal tendons of the patient when the apparatus is configured to be installed on the patient.

13. The apparatus of claim 1, wherein each of the one or more channels is textured and contoured so as not to promote adhesions or irritation of its respective tendon when the apparatus is installed on the patient.

14. The apparatus of claim 1, wherein the apparatus comprises a polymer coating.

15. The apparatus of claim 14, wherein the polymer coating is provided on the surface of the distal portion of the apparatus.

16. The apparatus of claim 1, wherein the distal portion defines a single position channel positioned and contoured to operatively receive one or more tendons of the patient.

17. The apparatus of claim 1, wherein the distal portion defines two channels positioned and contoured to operatively receive one or more tendons of the patient.

18. A method comprising:
placing the apparatus for distal fibula replacement according to claim 1 so that the proximal portion of the apparatus has anterior overlap with a portion of a fibula bone of a patient; and
placing one or more connectors through the apparatus so as to affix the apparatus to the portion of the fibula bone.

19. The apparatus of claim 1, wherein the anterior overlap formed by the proximal portion is configured to engage with a lateral portion of the fibula bone of the patient.

20. The apparatus of claim 1, wherein each of the one or more channels has an angle from superior posterior to distal anterior in the range of about 35 degrees to about 55 degrees.

* * * * *